(12) United States Patent
Fraser et al.

(10) Patent No.: US 11,459,524 B2
(45) Date of Patent: *Oct. 4, 2022

(54) FRAGRANCE COMPOSITION

(71) Applicant: TAKASAGO INTERNATIONAL CORPORATION, Tokyo (JP)

(72) Inventors: Stuart Fraser, Little Neston (GB); Johan Poncelet, Paris (FR); Barbara Renoud, Paris (FR); Jonathan Warr, Paris (FR)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/236,872

(22) Filed: Apr. 21, 2021

(65) Prior Publication Data

US 2021/0324298 A1    Oct. 21, 2021

(30) Foreign Application Priority Data

Apr. 21, 2020 (EP) .................................... 20305384

(51) Int. Cl.
*C11B 9/00* (2006.01)
(52) U.S. Cl.
CPC ............ *C11B 9/0007* (2013.01); *C11B 9/003* (2013.01)

(58) Field of Classification Search
None
See application file for complete search history.

(56) References Cited

U.S. PATENT DOCUMENTS

2017/0216164 A1    8/2017    Traynor et al.

FOREIGN PATENT DOCUMENTS

| CN | 110 452 774 A | 11/2019 |
|----|----|----|
| WO | WO 2009/123355 A2 | 10/2009 |

OTHER PUBLICATIONS

European Search Report dated Sep. 29, 2020 in Application No. EP 20305384.

*Primary Examiner* — Arrie L Reuther
(74) *Attorney, Agent, or Firm* — Baker Botts L.L.P.

(57) ABSTRACT

The present disclosure provides a fragrance accord comprising a mixture of dihydromyrcene and at least one compound selected from peppermint cyclohexanone, menthol, isopulegol, pulegol, menthyl acetate, and optionally at least one compound selected from citroxide, elemicin, elemol, geranic oxide, vanillyl ethyl ether, vanillyl butyl ether, caryophyllene beta, and zingiberene alpha. Consumer products containing said fragrance accord are also provided herein.

20 Claims, No Drawings

FRAGRANCE COMPOSITION

CROSS REFERENCE TO RELATED APPLICATIONS

This application claims priority to European Application No. 20 305 384.8 filed on Apr. 21, 2020, the contents of which are hereby incorporated by reference herein in its entirety.

FIELD

The present disclosure relates to a fragrance composition and to the use of said composition in various consumer products. More specifically the present disclosure relates to a fragrance composition which provides a cooling and/or a tingling effect.

BACKGROUND

There is a continuing interest in preparation of fragrance compositions and in use of such compositions in consumer products. Shortcomings of existing fragrance compositions can be limited intensity, noticeability, and perceptibility. For example, certain fragrance compositions can have appealing odors but can have limited intensity and high perception thresholds, which can limit the impact of the fragrance composition at distance from its source. Other fragrance compositions can have greater intensity and lower perception thresholds but can have less appealing odors. Moreover, fragrance compositions can become less noticeable due to a user's decrease in sensitivity over prolonged exposure. Adaptation and habituation can necessitate replacement of the fragrance source.

EP-A-3 219 332 discloses household products capable of delivering a perceived cooling sensation in the air, but without the product formulation coming into direct contact with the skin or mucous membranes of the consumer using the product. The product includes a fragrance composition containing from 0.2 to less than 10% by weight of isopulegol.

EP-A-3 219 333 discloses household products capable of delivering a perceived warming and/or tingling sensation through the air, but without the product formulation coming into direct contact with the skin or mucous membranes of the consumer using the product. The product includes a fragrance composition containing from 0.01 to less than 10% by weight of at least one compound selected from vanillyl ethyl ether, vanillyl n-propyl ether, vanillyl isopropyl ether, vanillyl butyl ether, elemol, elemicin, lime oxide, ocimene quintoxide, 2-isopropenyl-5-methyl-5-vinyltetrahydrofuran and isopulegol.

U.S.2018/0030373 A1 discloses a fragrance composition which includes one or more trigeminal-stimulating compounds including one or more of a cooling compound, a warming compound and/or a tingling compound. The examples in this patent application show the trigeminal-stimulating effect of a combination of (−)-menthol, vanillyl ethyl ether (HOTACT® VEE) and vanillyl butyl ether (HOTACT® VBE).

There is, however, a need from consumers for more fragrance compositions with inter alia stimulating effects, noticeable intensity, and/or perception thresholds. It has been found that when a specific mixture of fragrance compounds is added to a fragrance composition, the cooling and/or tingling effect of the fragrance composition is enhanced.

An object of the present disclosure therefore provides a fragrance composition deliverable by various consumer products, with appealing odors and improved adaptability and habituation thresholds.

SUMMARY

In one aspect, the present disclosure relates to a fragrance composition including from about 0.10 wt % to about 15.00 wt %, based on the weight of the fragrance composition, of an accord, wherein the accord includes (i) from about 90.00 wt % to about 100 wt %, based on the weight of the accord, of a mixture of dihydromyrcene (3,7-dimethylocta-1,6-diene, CAS 2436-90-0) and at least one other compound selected from the group consisting of peppermint cyclohexanone (2-sec butylcyclohexanone, CAS 14765-30-1), menthol (2-isopropyl-5-methylcyclohexan-1-ol, CAS 89-78-1), isopulegol (2-isopropenyl-5-methylcyclohexan-1-ol, CAS 7786-67-6), pulegol (2-isopropylidene-5-methylcyclohexan-1-ol, CAS 529-02-2) and menthyl acetate ((2-isopropyl-5-methylcyclohexyl)acetate, CAS 16409-45-3), and combinations thereof. In certain embodiments, the fragrance accord further includes (ii) from about 0.01 wt % to about 10.00 wt %, based on the weight of the accord, of at least one compound selected from the group consisting of citroxide (2,2-dimethyl-5-(1-methylpropen-1-yl)tetrahydrofuran, CAS 7416-35-5), elemicin (1,2,3 trimethoxy-5-prop-2-enyl benzene, CAS 487-11-6), elemol (2-(4-ethenyl-4-methyl-3-prop-1-en-2-yl-cyclohexyl)propanol, CAS 639-99-6), geranic oxide (2,2,6-trimethyl-6-vinyltetrahydropyran, CAS 7392-19-0), vanillyl ethyl ether (4-(ethoxymethyl)-2-methoxyphenol, CAS 13184-86-6), vanillyl butyl ether (4-(butoxymethyl)-2-methoxyphenol, CAS 82654-98-6), caryophyllene beta (11R-(1R,4E,9S)-4,11,11-trimethyl-8-methylenebicyclo7.2.0)undece-4-ene, CAS 87-44-5) and zingiberene alpha ((5R)-2-methyl-5-[(2S)-6-methylhept-5ene-2yl]cyclohexa-1,3-diene, CAS 495-60-3), and combination thereof. In certain embodiments, the sum of (i)+(ii) makes up 100 wt % of the accord.

In certain embodiments, the fragrance composition can include from about 1.00 wt % to about 12.00 wt % of the accord. In certain other embodiments, the fragrance composition can include from about 2.00 wt % to about 10.00 wt % of the accord.

In certain embodiments, the accord comprises at least about 5.00 wt % of dihydromyrcene, based on the weight of the accord.

In certain embodiments, the mixture (i) can include dihydromyrcene and peppermint cyclohexanone.

In certain embodiments, the accord can include at least about 40.00 wt % of dihydromyrcene and peppermint cyclohexanone, based on the weight of the accord.

In certain embodiments, the mixture (i) can include dihydromyrcene and menthol.

In certain embodiments, the accord can include at least about 40.00 wt % of dihydromyrcene and menthol, based on the weight of the accord.

In certain embodiments, the at least one compound (ii) is selected from citroxide, elemicin, elemol and mixtures thereof.

In certain embodiments, the accord can include citroxide. In certain particular embodiments, citroxide is present in the accord in an amount of from about 0.01 wt % to about 1.00 wt %, based on the weight of the accord.

In certain embodiments, the accord can include dihydromyrcene, peppermint cyclohexanone, and citroxide.

In certain other embodiments, the accord can include dihydromyrcene, menthol, and citroxide.

In certain embodiments, the fragrance composition is encapsulated. In certain other embodiments, the fragrance composition is not encapsulated.

In certain embodiments, the present disclosure provides a consumer product comprising the fragrance composition as disclosed herein. In certain embodiments, the consumer product is a household product, a laundry product, a personal care product or a cosmetic product. In certain embodiments, the household product is an air freshener dispenser device, a floor cleaner or a solid or a liquid toilet rim block. In certain particular embodiments the household product is an air freshener dispenser device.

In certain embodiments, the laundry product is a laundry detergent, a laundry additive, a fabric conditioner or a fabric softener.

In certain embodiments, the present disclosure is also directed to a method to enhance intensity and/or the cooling effect and/or the tingling effect of a fragrance composition, the method comprising adding to the fragrance composition a fragrance accord, as disclosed herein. In certain particular embodiments, the fragrance accord can include (i) from about 90.00 wt % to about 100 wt %, based on the weight of the accord, of a mixture of dihydromyrcene and at least one other compound selected from the group consisting of peppermint cyclohexanone, menthol, isopulegol, pulegol and menthyl acetate. In certain embodiments, the fragrance accord can further include (ii) from about 0.01 wt % to about 10.00 wt %, based on the weight of the accord, of at least one compound selected from the group consisting of citroxide, elemicin, elemol, geranic oxide, vanillyl ethyl ether, vanillyl butyl ether, caryophyllene beta and zingiberene alpha, wherein the sum of (i)+(ii) makes up 100 wt % of the accord.

In another aspect, the present disclosure relates to the use of an accord as defined above for enhancing the intensity and/or the cooling effect and/or the tingling effect of a fragrance composition.

DETAILED DESCRIPTION

As used herein, the use of the word "a" or "an" when used in conjunction with the term "comprising" in the claims and/or the specification can mean "one," but it is also consistent with the meaning of "one or more," "at least one," a plurality, and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the terms "include", "includes" and "including" are meant to be synonymous with the phrase "including but not limited to".

As used herein, the term "accord" refers to a mixture of at least two compounds which can induce a variety of different sensations such as tingling, warming, and/or cooling. One or more "accords" can be utilized as part of fragrance composition.

As used herein, the term "habituation" refers to a user or tester's long-term loss of awareness of a background odour. Habituation can be considered a form of learning that can arise from prolonged exposure to an odour. Habituation can be related to adaptation. Like adaptation, habituation can result in lower sensitivity to an odour, as a lower level of attention is directed to the odour.

As used herein, the term "consumer product" or "end product" refers to a composition that is in a form ready for use by the consumer for the marketed indication. A solvent suitable for use in a consumer product is a solvent that, when combined with other components of the end product, will not render the consumer product unfit for its intended consumer use.

In the context of the application, the various embodiments described in the various aspects of the present disclosure can be combined.

In one aspect, the present disclosure relates to a fragrance composition including from about 0.10 wt % to about 15.00 wt %, based on the weight of the fragrance composition, of an accord including:

(i) from about 90.00 wt % to about 100 wt %, based on the weight of the accord, of a mixture of dihydromyrcene and at least one other compound selected from peppermint cyclohexanone, menthol, isopulegol, pulegol and menthyl acetate;

(ii) from about 0 wt % to about 10.00 wt %, based on the weight of the accord, of at least one compound selected from citroxide, elemicin, elemol, geranic oxide, vanillyl ethyl ether, vanillyl butyl ether, caryophyllene beta and zingiberene alpha;

wherein the sum of (i)+(ii) makes up 100 wt % of the accord.

In certain embodiments, the accord includes from about 90.00 wt % to about 100 wt %, from about 92.00 wt % to about 100 wt %, from about 95.00 wt % to about 100 wt % from about 98.00 wt % to about 100 wt % based on the weight of the accord, of a mixture of dihydromyrcene and at least one other compound selected from peppermint cyclohexanone, menthol, isopulegol, pulegol and menthyl acetate. In certain embodiments, the accord includes about 90.00 wt %, about 92.00 wt %, about 95.00 wt %, about 98.00 wt % or about 100 wt % based on the weight of the accord, of a mixture of dihydromyrcene and at least one other compound selected from peppermint cyclohexanone, menthol, isopulegol, pulegol and menthyl acetate.

In certain embodiments, the accord includes from about 0.01 wt % to about 10.00 wt %, from about 0.50 wt % to about 10.00 wt %, from about 1.00 wt %, to about 10.00 wt %, from about 1.50 wt %, to about 10.00 wt %, from about 2.00 wt %, to about 10.00 wt %, from about 2.50 wt %, to about 10.00 wt %, from about 5.00 wt %, to about 10.00 wt %, from about 7.50 wt %, to about 10.00 wt %, from about 9.00 wt %, to about 10.00 wt %, from about 0.01 wt % to about 9.00 wt %, from about 0.01 wt % to about 7.50 wt %, from about 0.01 wt % to about 5.00 wt %, from about 0.01 wt % to about 2.50 wt %, from about 0.01 wt % to about 1.50 wt %, from about 0.01 wt % to about 1.00 wt %, based on the weight of the accord, of at least one compound selected from citroxide, elemicin, elemol, geranic oxide, vanillyl ethyl ether, vanillyl butyl ether, caryophyllene beta and zingiberene alpha.

In certain embodiments, the amount of dihydromyrcene and at least one other compound selected from peppermint cyclohexanone, menthol, isopulegol, pulegol and menthyl acetate makes up 100 wt % of the accord.

In one embodiment, the fragrance composition includes from about 1.00 wt % to about 12.00 wt %, from about 2.00 wt % to about 10.00 wt %, from about 3.00 wt % to about 9.00 wt %, or from about 4.00 wt % to about 9.00 wt %, of the accord, based on the weight of the fragrance composition.

In one embodiment, the accord includes about 92.00 wt % to about 100 wt %, for example 93.00 wt %, 94.00 wt %, 95.00 wt %, 96.00 wt %, 97.00 wt %, 98.00 wt %, or 99.00 wt % of the mixture of compounds defined under (i). In this case the accord includes from about 0.00 wt % to about 8.00 wt %, for example 1.00 wt %, 2.00 wt %, 3.00 wt %, 4.00 wt %, 5.00 wt %, 6.00 wt % or 7.00 wt %, of one or more compounds defined under (ii).

In certain embodiments, the mixture defined under (i) includes dihydromyrcene and peppermint cyclohexanone. In certain particular embodiments, the mixture defined under (i) consists of dihydromyrcene and peppermint cyclohexanone.

In certain embodiments, the mixture defined under (i) includes, dihydromyrcene and menthol. In certain particular embodiments, the mixture defined under (i) consists of dihydromyrcene and menthol.

In certain embodiments, the mixture defined under (i) includes dihydromyrcene and isopulegol. In certain particular embodiments, the mixture defined under (i) consists of dihydromyrcene and isopulegol.

In certain embodiments, the at least one compound defined under (ii) is selected from citroxide, elemicin, elemol and mixtures thereof. In a certain particular embodiment, the at least one compound defined under (ii) is citroxide.

In certain embodiments, the accord includes at least about 5.00 wt %, at least about 10.00 wt %, or at least about 15.00 wt % of dihydromyrcene, based on the weight of the accord.

In certain embodiments, the accord includes at least about 40.00 wt %, at least about 50.00 wt %, or at least about 60.00 wt %, of dihydromyrcene and peppermint cyclohexanone, of based on the weight of the accord.

In certain embodiments, the accord includes at least about 40.00 wt %, at least about 50.00 wt %, or at least about 60.00 wt %, of dihydromyrcene and menthol, based on the weight of the accord.

In certain embodiments, the accord includes citroxide, and citroxide represents less than about 1.00 wt % of the accord, such as, but not limited to from about 0.01 to about 1.00 wt %, or from about 0.01 wt % to about 0.5 wt %, of the accord.

In certain embodiments, the accord includes dihydromyrcene, peppermint cyclohexanone and citroxide. In a certain particular embodiment, the accord consists of dihydromyrcene, peppermint cyclohexanone and citroxide.

In certain embodiments, the accord includes dihydromyrcene, menthol, and citroxide. In a certain particular embodiments, the accord consists of dihydromyrcene, menthol, and citroxide.

Dihydromyrcene is derived from pine distillates and widely used as an intermediate for other syntheses. It exists as two stereoisomers (+) and (−) dihydromyrcene and is also known as citronellene. Dihydromyrcene is one of the components of Dimene, a product which is available from the company Bordas. Other fragrance compounds can also provide a source for dihydromyrcene. The content of dihydromyrcene in Dimene typically ranges from about 20.00 wt % to about 45.00 wt %. All stereoisomeric forms of dihydromyrcene are within the scope of the present application.

Peppermint cyclohexanone is commercially available as Freskomenthe®.

Isopulegol is available either as a racemic mixture (CAS 7786-67-6), or as the (−)-isomer (CAS 89-79-2). In one embodiment isopulegol is available as Coolact® P, a product from Takasago. Isopulegol can have an optical isomer and chemical purity of greater than 90%, greater than 95%, greater than 97.5%, or greater than 99%. Isopulegol purity is determined by gas chromatography using the method described in U.S. Pat. No. 5,773,410 by summing the area percent of impurity peaks and subtracting these from the total measured area which is taken to be 100%.

Menthol is available either as the racemate (CAS 89-78-1) or as the (−) isomer (CAS 2216-51-5), the latter being the main form occurring in nature.

Citroxide, also known as ocimene quintoxide, is one of the components of lime oxide (CAS 73018-51-6) which is commercially available e.g., from the company Ventos or the company Givaudan. The content of citroxide in lime oxide typically ranges from about 5.00 wt % to about 20.00 wt %. All stereoisomeric forms of citroxide are within the scope of the present application.

Geranic oxide, also known as limetol, is commercially available from e.g., the company Givaudan.

Elemol and elemicine are components notably but not exclusively of elemi oil. Caryophyllene beta is a component of pepper oil. Zingiberene alpha is a component of ginger oil.

In certain embodiments, the fragrance composition includes, in addition to the accord described above, one or more fragrance compounds. In certain embodiments, the fragrance composition can include at least two, at least five, or at least eight distinct fragrance compounds. In certain embodiments, the fragrance composition can include highly complex mixtures of fragrance compounds, chosen to provide any desired odour. In the context of the present disclosure the term "fragrance" is intended to be synonymous with "perfume". Fragrance compounds typically used in the field of perfumery and suitable for the purposes of the present disclosure are described more fully in S. Arctander, Perfume Flavors and Chemicals 1969, Vols. I and II, Montclair, N.J. and in The Merck Index, 8$^{th}$ edition, Merck & Co., Inc. Rahway, N.J. The term "fragrance compound" encompasses naturally occurring as well as synthetic materials known for use in perfumes, as well as animal oils. A fragrance compound can also be any natural oil or extract, or chemical compound used in a fragrance composition. Natural oils and extracts are described in The Essential Oils by E Guenther published in 1949 by Van Nostrand and can include extracts, pressings, collection of exudates, and distillates from any part of suitable plants: roots, rhizomes, bulbs, corms, stem, bark, heartwood, leaves, flowers, seeds and fruit. Examples of such extracts and distillates include citrus fruit oils such as orange, mandarin, grapefruit, lime or lemon oils, tree oils such as pine, or cedarwood, herb oils such as peppermint, thyme, lavender, basil, rosemary, clove or flower extracts such as rose, jasmine, muguet, or geranium oil.

In certain embodiments, each fragrance compound has a molecular weight greater than 100 g/mol, greater than 120 g/mol and lower than 325 g/mol, or lower than 300 g/mol. In certain other embodiments, each fragrance compound has a boiling point in the range 80-400° C., such as in the range 100-350° C., when measured at 760 mm Hg.

Advantageously, the fragrance compounds are selected from the following list:

$C_8$-$C_{18}$ hydrocarbons, such as but not limited to delta-3-carene, alpha-pinene, beta-pinene, alpha-terpinene, gamma-terpinene, p-cymene, bisabolene, camphene, cedrene, farnesene, limonene, longifolene, myrcene, ocimene, valencene, (E,Z)-1,3,5-undecatriene;

$C_2$-$C_{18}$ aliphatic alcohols, such as but not limited to hexanol, octanol, 3-octanol, 2,6-dimethylheptanol, 2-methylheptanol, 2-methyloctanol, (E)-3-hexenol, (E) and (Z)-3-hexenol, 1-octen-3-ol, mixtures of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol;

$C_2$-$C_{18}$ aliphatic aldehydes and their acetals, such as but not limited to hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal diethyl acetal, 1,1-dimethoxy-2,2,5-trimethyl-4-hexene, citronellyl oxyacetaldehyde;

$C_3$-$C_{18}$ aliphatic ketones and oximes thereof, such as but not limited to 2-heptanone, 2-octanone, 3-octanone, 2-nonanone, 5-methyl-3-heptanone, 5-methyl-3-heptanone oxime, 2,4,4,7-tetramethyl-6-octen-3-one;

$C_2$-$C_{18}$ aliphatic sulphur-containing compounds, such as but not limited to 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol;

$C_2$-$C_{18}$ aliphatic nitrile-containing compounds, such as but not limited to 2-nonenenitrile, 2-tridecenenenitril e, 2,12-tridecenene-nitrile, 3,7-dimethyl-2,6-octadienenitrile, 3, 7-dimethyl-6-octenenitrile;

$C_2$-$C_{18}$ aliphatic carboxylic acids and esters thereof, such as but not limited to (E)- and (Z)-3-hexenyl formate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexyl butyrate, (E)- and (Z)-3-hexenyl isobutyrate, hexyl crotonate, ethyl isovalerate, ethyl 2-methylpentanoate, ethyl hexanoate, allyl hexanoate, ethyl heptanoate, allyl heptanoate, ethyl octanoate, ethyl (E,Z)-2,4-decadienoate, methyl 2-octynoate, methyl 2-nonynoate, allyl-2-isoamyloxyacetate, methyl-3,7-dimethyl-2,6-octadienoate;

$C_4$-$C_{18}$ acyclic terpene alcohols, such as but not limited to citronellol, geraniol, nerol, linalool, lavandulol, nerolidol, farnesol, tetrahydrolinalool, tetrahydrogeraniol, 2,6-dimethyl-7-octen-2-ol, 2,6-dimethyloctan-2-ol, 2-methyl-6-methylene-7-octen-2-ol, 2,6-dimethyl-5,7-octadien-2-ol, 2,6-dimethyl-3,5-octadien-2-ol, 3,7-dimethyl-4,6-octadien-3-ol, 3,7-dimethyl-1,5,7-octatrien-3-ol, 2,6-dimethyl-2,5,7-octatrien-1-ol;

$C_4$-$C_{18}$ acyclic terpene aldehydes and ketones, such as but not limited to geranial, neral, citronellal, 7-hydroxy-3,7-dimethyloctanal, 7-methoxy-3,7-dimethyloctanal, 2,6,10-trimethyl-9-undecenal, geranylacetone, and the dimethyl and diethyl acetals of geranial, neral, 7-hydroxy-3,7-dimethyloctanal;

$C_4$-$C_{18}$ cyclic terpene alcohols, such as but not limited to alpha-terpineol, terpineol-4, menthan-8-ol, menthan-1-ol, menthan-7-ol, borneol, isoborneol, linalool oxide, nopol, cedrol, ambrinol, vetiverol, guaiol;

$C_4$-$C_{18}$ cyclic terpene aldehydes and ketones, such as but not limited to fenchone, alpha-ionone, beta-ionone, alpha-n-methylionone, beta-n-methylionone, alpha-isomethylionone, beta-isomethylionone, alpha-irone, alpha-damascone, beta-damascone, beta-damascenone, delta-damascone, gamma-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H)-one, nootkatone, dihydronootkatone, alpha-sinensal, beta-sinenal, methyl cedryl ketone;

$C_4$-$C_{18}$ cyclic alcohols, such as but not limited to 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol;

$C_4$-$C_{18}$ cycloaliphatic alcohols, such as but not limited to alpha-3,3-trimethylcyclohexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)-pentan-3-ol, 1-(2,2,6-trimethylcyclohexyl)hexan-3-ol;

$C_4$-$C_{18}$ cyclic and cycloaliphatic ethers, such as but not limited to cedryl methyl ether, cyclododecyl methyl ether, (ethoxymethoxy)cyclododecane, alpha-cedrene epoxide, 3a,6,6,9a-tetramethyl-dodecahydronaphtho[2,1-b]furan, 3a-ethyl-6, 6,9a-trimethyl dodecahydronaphtho[2,1-b]furan, 1,5,9-trimethyl-13-oxabicyclo[10.1.0]trideca-4,8-diene, rose oxide, 2-(2,4-dimethyl-3-cyclohexen-1-yl)-5-methyl-5-(1-methylpropyl)-1,3-dioxane;

$C_4$-$C_{18}$ cyclic ketones, such as but not limited to 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-1-one, 6,7-dihydro-1,1,2,3,3-pentamethyl-4(5H)-indanone, 9-cycloheptadecen-1-one, cyclopentadecanone, cyclohexadecanone;

$C_4$-$C_{18}$ cycloaliphatic aldehydes, such as but not limited to 2,4-dimethyl-3-cyclohexenecarbaldehyde, 2-methyl-4-(2,2,6-trimethyl-cyclohexen-1-yl)-2-butenal, 4-(4-hydroxy-4-methylpentyl)-3-cyclohexenecarbaldehyde, 4-(4-methyl-3-penten-1-yl)-3-cyclohexenecarbaldehyde;

$C_4$-$C_{18}$ cycloaliphatic ketones, such as but not limited to 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphthalenyl methyl ketone, methyl-2,6,10-trimethyl-2,5,9-cyclododecatrienyl ketone, tert-butyl(2,4-dimethyl-3-cyclohexen-1-yl)ketone;

esters of cyclic alcohols in $C_4$-$C_{18}$, such as but not limited to 2-tert-butylcyclohexyl acetate, 4-tert-butyl-cyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl isobutyrate, 4,7-methanooctahydro-5 or 6-indenyl acetate;

esters of cycloaliphatic carboxylic acids in $C_4$-$C_{18}$, such as but not limited to allyl 3-cyclohexylpropionate, allyl cyclohexyloxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

$C_4$-$C_{18}$ aromatic hydrocarbons, such as but not limited to styrene and diphenylmethane;

$C_4$-$C_{18}$ araliphatic alcohols, such as but not limited to benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

esters of araliphatic alcohols in $C_4$-$C_{18}$ and aliphatic carboxylic acids in $C_4$-$C_{18}$, such as but not limited to benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, alpha-trichloromethylbenzyl acetate, alpha,alpha-dimethylphenylethyl acetate, alpha,alpha-dimethylphenylethyl butyrate, cinnamyl acetate, 2-phenoxyethyl isobutyrate, 4-methoxybenzyl acetate;

$C_2$-$C_{18}$ araliphatic ethers, such as but not limited to 2-phenylethyl methyl ether, 2-phenylethyl isoamyl ether, 2-phenylethyl 1-ethoxyethyl ether, phenylacetaldehyde dimethyl acetal, phenylacetaldehyde diethyl acetal, hydratropaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

$C_4$-$C_{18}$ aromatic and araliphatic aldehydes, such as but not limited to benzaldehyde, phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert.-butylphenyl) propanal, 3-(4-tert-butylphenyl)propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylenedioxybenzaldehyde, 3,4-dimethoxybenzaldehyde, 2-methyl-3-(4-methoxyphenyl)propanal, 2-methyl-3-(4-methylenedioxyphenyl)propanal;

$C_4$-$C_{18}$ aromatic and araliphatic ketones, such as but not limited to acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methylethyl)-1H-5-indenyl]ethanone, 5',6',7',8'-tetrahydro-3',5',5',6',8',8'-hexamethyl-2-acetonaphthone;

$C_4$-$C_{18}$ aromatic and araliphatic carboxylic acids and esters thereof, such as but not limited to phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

nitrogen-containing aromatic compounds in $C_4$-$C_{18}$, such as but not limited to 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenenitrile, 5-phenyl-3-methylpentanenitrile, methyl anthranilate, methyl N-methylanthranilate, Schiff bases of methyl anthranilate with 7-hydroxy-3,7-dimethyloctanal, 2-methyl-3-(4-tert-butylphenyl)propanal, 2,4-dimethyl-3-cyclohexene-carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

phenols, phenyl ethers and phenyl esters, such as but not limited to estragole, anethole, eugenol, eugenyl methyl ether, isoeugenol, isoeugenyl methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

heterocyclic compounds in $C_4$-$C_{12}$, such as but not limited to 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

lactones in $C_4$-$C_{18}$, such as but not limited to 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene 1,12-dodecanedioate, ethylene 1,13-tridecanedioate, coumarin, 2,3-dihydrocoumarin, octahydrocoumarin.

In certain embodiments, the fragrance compounds present in the fragrance composition do not contain ionizing functional groups, such as sulfonates, sulphates, phosphates or quaternary ammonium ions.

In certain embodiments, the fragrance composition of the present disclosure can include one or more support materials, such as solvents or UV stabilizers. Examples of suitable solvents include hydrocarbons such as those sold under the trade name Isopar®; ethers such as those sold under the Dowanol® trade name; benzyl benzoate; isopropyl myristate; dialkyl adipates; dialkyl succinates; dialkyl glutarates such as the dimethyl esters sold under the trade name Flexisolv®; citrate esters, such as triethyl citrate and acetyl tributyl citrate; soybean methyl ester such as ME-S1885 (sold by Peter Cremer NA); diethyl phthalate; diethylene glycol monoethyl ether; 3-methoxy-3-methyl-1-butanol;

dipropylene glycol; and isopropylidene glycerol sold under the Augeo® Clean Multi brand name. Examples of UV stabilisers include butyl methoxy dibenzoyl methane; bis ethylhexyloxyphenolmethoxyphenyl triazine; those sold under the Uvinol® trade name such as Uvinul D50 [bis(2, 4-dihydroxyphenyl)-methanone], Uvinul MC80 (ethylhexyl methoxycinnamate) and Uvinul M40 (benzophenone-3); those sold under the Parsol® trade name, such as Parsol® MCX (same product as Uvinul MC80) and Parsol® 1789 (butyl methoxydibenzoylmethane); and those sold under the Tinogard® trade name, such as Tinogard® TT (pentaerythrityl tetra di-t-butyl hydroxyhydrocinnamate).

The fragrance composition can be used as such, i.e., as a free fragrance composition, or else can be included in a delivery system, which system can in turn be incorporated into various consumer products with the view of eventually delivering a noticeable odour to the consumer. Non-limiting examples of delivery systems include starch capsules, silica capsules and core shell capsules.

General descriptions and methods of preparation of microcapsules can be found in "MICROENCAPSULATION: Methods and Industrial Applications Edited by Benita and Simon (Marcel Dekker, Inc. 1996)". Microcapsules are also described in Kirk Othmer's Encyclopedia of Chemical Technology 5th edition. Capsules can be formed by mechanical or chemical means. Mechanically formed capsules can be formed by means, such as spray chilling e.g., in U.S. 2004/0106536, by compression of solids or by spray drying emulsions e.g., in U.S. Pat. No. 6,200,949. Chemically formed capsules are produced by chemical reactions forming ionic or covalent bonds using techniques such as co-acervation, interfacial polymerisation, condensation reactions and free radical polymerisation. One particularly efficient and commercially important type of microcapsule is referred to as a wall or shell or core shell microcapsule, and includes a generally spherical shell of water- and oil-insoluble materials, typically a network polymer material, within which fragrance or other hydrophobic material is contained. It can be understood that these various methods of encapsulation can be combined as can the different chemical reactions used to prepare capsule walls. Encapsulation can combine physical and chemical means of capsule preparation or combine more than one type of chemical reaction to prepare multi walled capsules or hybrid capsule walls. Capsules can also be obtained by co-acervation methods. More specific descriptions of such methods can be found in U.S. Pat. Nos. 2,800,457; 2,800,458, 3,041,288 and WO 99/17871. Descriptions of interfacial polymerisation methods can be found in U.S. Pat. Nos. 4,681,806; 3,415,758; 8,426,353; U.S. 2008/020629 and EP-A-2 038 053. Examples of capsules formed by condensation reactions can be found in U.S. Pat. Nos. 3,516,941; 3,516,846; 6,261,483; U.S. 2004/087477; GB-A-2,073,132 and EP-A-1 393 706. Capsules formed by free radical polymerisation are described in U.S. Pat. Nos. 6,849,591; 6,951,836 and U.S. 2010/002860.

In certain embodiments, the fragrance composition is encapsulated in core shell capsules, i.e., capsules having a core (including, such as consisting essentially of, the fragrance composition) surrounded by a shell which can be made from various materials.

In certain embodiments, the shell of the microcapsules includes a material selected from polyolefins such as polyethylenes, polyamides, polystyrenes, polyisoprenes, polycarbonates, polyesters, polyacrylates, polyurethanes, aminoplasts, polysaccharides such as alginate and/or chitosan, gelatine, shellac, epoxy resins, vinyl polymers, water insoluble inorganics, silicone, and mixtures thereof.

In certain embodiments, the shell of the microcapsules includes urea-formaldehyde, melamine formaldehyde or cross-linked melamine formaldehyde.

In certain embodiments, the shell of the microcapsules includes a polyacrylate. Non-limiting examples of polyacrylate shells are disclosed e.g., in EP-A-2 620 211, EP-A-2 832 440, EP-A-2 832 441 and EP-A-2 832 442, the content of which is incorporated by reference.

In certain embodiments, the shell of the microcapsules includes the reaction product of a Michael donor and a Michael acceptor, wherein the reaction is optionally carried out in the presence of solid colloidal particles and/or a catalyst. For example, the shell can include the reaction product of (i) an α,β-unsaturated carbonyl compound and a multifunctional amine, optionally in the presence of solid colloidal particles; or (ii) an α,β-unsaturated carbonyl compound and a multifunctional thiol compound, optionally in the presence of a catalyst.

In certain embodiments the shell of the microcapsules includes the reaction product of a multifunctional isocyanate and a multifunctional thiol compound, optionally in the presence of solid colloidal particles and/or a catalyst.

In certain embodiments, the shell of the microcapsules is as defined in WO 2019/121736, WO 2019/121738, WO 2020/020829 or else KR 20190023697.

In certain other embodiments, the shell of the microcapsules is as defined in European patent applications number 20305187.5, 20305188.3 or else 20305189.1, the content of which is incorporated by reference.

In certain embodiments, a deposition aid is coated on the shell of the microcapsules to increase deposition or adhesion of the microcapsules to various surfaces such as various substrates including but not limited to paper, fabric skin, hair, towels, or other surfaces. Suitable deposition aids include poly(acrylamide-co-diallyldimethylammonium) chloride, poly(diallyldimethylammonium) chloride, polyethylenimine, cationic polyamine, poly[(3-methyl-1-vinylimidazolium chloride)-co-(1-vinylpyrrolidone)], copolymer of acrylic acid and diallyldimethylammonium chloride, cationic guar, guar gum, an organopolysiloxane such as described in U.S. patent application 2015/0030557. Deposition aids can also be selected from poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone-vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinylpyrrolidone/methacrylamidopropyltrimethylammonium chloride), polyvinylpyrrolidone/vinyl acetate, polyvinyl pyrrolidone/ dimethylaminoethyl methacrylate, polyvinyl amines, polyvinyl formamides, polyallyl amines and copolymers of polyvinyl amines, polyvinyl formamides, and polyallyl amines, and mixtures thereof.

The free or encapsulated fragrance compositions disclosed herein can advantageously be incorporated into a variety of products. When encapsulated the microcapsules are advantageously prepared as a dispersion, which dispersion is then incorporated into the desired product.

Accordingly, another aspect of the present disclosure relates to a product including a free or encapsulated fragrance composition as disclosed above. The product can be a non-edible consumer goods product, a household cleaner or laundry product, a personal cleansing product or a cosmetic product.

Unless otherwise indicated, non-edible means non-intended for ingestion by humans or animals. This includes non-food products that can accidentally be swallowed during normal use. Notably, included within the definition of non-edible products are products for dental and oral care, such as toothpastes, mouth washes and lip balms which although not intended for ingestion can nevertheless accidentally enter the gastro-intestinal tract.

The formulations and ingredients of liquid household, laundry, personal care and cosmetic products in which the dispersion of microcapsules of the present disclosure can be used are well known to those skilled in the art, reference can be made to the following works:

Formulating Detergents and Personal Care Products A guide to Product Development by L Ho Tan Tai, ISBN 1-893997-10-3 published by the AOCS Press, Volume 67 of the Surfactant Science Series Liquid Detergents ISBN 0-8247-9391-9 (Marcel Dekker Inc), Volume 71 of the Surfactant Science Series Liquid Detergents ISBN 0-8247-9988-7 (Marcel Dekker Inc), Harry's Cosmeticology published by CHS Press 8th Edn. 2000 ISBN 0820603724, Woollatt, 'The Manufacture of Soaps, Other Detergents and Glycerine', John Wiley & Sons, 1985.

Personal care and cosmetic products include products that can be applied to the skin, hair and nails, either as leave on or rinse off product. In the context of the present disclosure "rinse-off" means that the intended product use includes application to skin and/or hair followed by rinsing and/or wiping the product from the skin and/or hair within a few seconds to minutes of the application step. Personal care and cosmetic products include powders, creams, emulsions, lotions, gels and oils for the skin (face, hands, feet etc), tinted bases (liquids and pastes) and liquid impregnated tissues; products for applying and removing make-up from the face and eyes; hair care products including hair tints and bleaches; products for waving, straightening, setting and fixing hair; shaving products including creams, foams mousses and depilatory products; sun bathing products and products for tanning without the sun; deodorant and antiperspirant products.

In certain embodiments a personal care or cosmetic product is selected from the group consisting of a shaving aid, a shampoo, a hair-conditioner product, a leave-on-skin-care product, a skin cleansing or washing product (such as a rinse-off skin cleansing or washing product), a moist tissue and a body spray, deodorant or antiperspirant.

Shaving aids specifically include foams, gels, creams and bars (reference can be made for example to U.S. Pat. Nos. 7,069,658, 6,944,952, 6,594,904, 6,182,365, 6,185,822, 6,298,558 and 5,113,585).

Shampoos and hair conditioners specifically include two-in-one shampoos and shampoos especially formulated for dry or greasy hair or containing additives such as antidandruff agents. Hair conditioners can be rinse off or leave on hair conditioners also included are hair tonics, bleaches colorants, setting and styling products. Reference can be made for example to U.S. Pat. Nos. 6,162,423, 5,968,286, 5,935,561, 5,932,203, 5,837,661, 5,776,443, 5,756,436, 5,661,118, 5,618,523.

Leave-on-skin-care products include Eau de Parfum, Eau de toilette, colognes, moist tissues, body sprays, deodorants and antiperspirants.

Skin washing products specifically include beauty and hygiene bar soaps, shower gels, liquid soaps, body washes, exfoliating gels and pastes (reference can be made for example to U.S. Pat. Nos. 3,697,644; 4,065,398; 4,387,040).

Moist tissues (wipes) specifically include skin cleansing wipes, baby wipes, make-up removal wipes and skin refreshing wipes (reference can be made for example to U.S. Pat. No. 4,775,582; WO 02/07701; WO 2007/069214 and WO 95/16474).

Body sprays, deodorants and antiperspirants specifically include sticks, liquid roll-on applicators and pressurized sprays.

Household products include hard surface cleaners such as cleaners for floors, solid work surfaces, tiled surfaces, crockery by hand or machine washing and mirrors and glass; and soft furnishing treatments such as liquid cleaners and refresher products such as odour treatment agents as exemplified by Febreze® (P&G). Household cleaners can be in the form of cream cleaners, isotropic liquid cleaners, spray cleaners and pre-moistened surface cleaning wipes (reference can be made for example to WO 91/08283, EP 743 280, WO 96/34938, WO 01/23510, and WO 99/28428). Spray cleaners can be dispensed from a trigger sprayer or aerosol sprayer, as are well known in the art. An aerosol sprayer dispenses the product using propellant pressure, while a trigger sprayer dispenses the product by pumping it under manual actuation. A suitable aerosol dispenser can have a dip tube or bag on valve, according to U.S. 2015/0108163 and/or U.S. 2011/0303766. A suitable trigger sprayer is found in U.S. Pat. No. 8,322,631.

Household products also include freshening composition which can be used in a device for the delivery of a volatile material to the atmosphere or on inanimate surfaces (e.g., fabric surfaces as a fabric refresher). Such device can be configured in a variety of ways.

For example, the device can be configured for use as an energized air freshener (i.e., powered by electricity; or chemical reactions, such as catalyst fuel systems; or solar powered; or the like). Exemplary energized air freshening devices include a powered delivery assistance means which can include a heating element, fan assembly, or the like. More particularly, the device can be an electrical wall-plug air freshener as described in U.S. Pat. No. 7,223,361; a battery (including rechargeable battery) powered air freshener having a heating and/or fan element. In energized devices, the volatile material delivery engine can be placed next to the powered delivery assistance means to diffuse the volatile perfume material. The volatile perfume material can be formulated to optimally diffuse with the delivery assistance means.

The device can also be configured for use as a non-energized air freshener. An exemplary non-energized air freshener includes a reservoir and, optionally, capillary or wicking means or an emanating surface, to help volatile materials passively diffuse into the air (i.e., without an energized means). A more specific example includes a delivery engine having a liquid reservoir for containing a volatile material and a microporous membrane enclosing the liquid reservoir as disclosed in U.S. Pat. Nos. 8,709,337 and 8,931,711.

The device can also be configured for use as an aerosol sprayer or a non-aerosol air sprayer including traditional trigger sprayers as well as trigger sprayer having a pre-compression and/or buffer system for fluid therein. In this embodiment, the delivery engine can deliver volatile materials upon user demand or programmed to automatically deliver volatile materials to the atmosphere.

The device can also be configured for use with an air purifying system to deliver both purified air and volatile materials to the atmosphere. Non-limiting examples include air purifying systems using ionization and/or filtration technology for use in small spaces (e.g., bedrooms, bathrooms, automobiles, etc.), and whole house central air conditioning/heating systems.

Household products further include absorbent articles, such as a sanitary paper product, said sanitary paper product including one or more layers of conventional felt-pressed tissue paper, conventional wet-pressed tissue paper, pattern densified tissue paper, starch substrates, high bulk, uncompacted tissue paper and mixtures thereof. In certain embodiments, said absorbent article includes an absorbent core, and optionally a backsheet, topsheet, acquisition layer or outer wrapper, wherein the microcapsules of the present disclosure are disposed on the absorbent core or between one or more of the optional layers. The absorbent article can be contained in a polybag or paper carton. The absorbent article can further include a lotion. The absorbent article can further include one or more adjunct ingredients selected from surfactants, inks, dyes, mineral oils, petrolatum, polysiloxanes, cyclodextrins, clays, silicates, aluminates, vitamins, isoflavones, flavones, metal oxides, short chain organic acids ($C_1$-$C_8$), triglycerides ($C_8$-$C_{22}$), and antioxidants.

Laundry products include powdered laundry detergents, detergent tablets and bars, laundry detergent liquids include light duty liquids, heavy duty liquids, concentrated liquid detergents, non or low aqueous laundry liquids and more specialised cleaners for woollen or dark garments; and fabric softeners and pre- and post-wash treatments such as tumble drier sheets, ironing waters and wash additives such as the Lenor Unstoppables™ from Procter and Gamble.

In one embodiment a laundry product is selected from the group consisting of a fabric softener, a fabric conditioner and a laundry detergent.

Fabric softeners and conditioners specifically include both conventional diluted (e.g., 2% to 8% by weight of softener in the product) liquid active concentration softeners and concentrated (e.g., 10% to 40% by weight of softener in the product) liquid active concentration softeners as well as fabric conditioners which can contain ingredients to protect colors or garment shape and appearance (reference can be made for example to U.S. Pat. Nos. 6,335,315, 5,674,832, 5,759,990, 5,877,145, 5,574,179).

Laundry detergents, particularly liquid laundry detergents, specifically include light duty liquid detergents and heavy-duty liquid detergents which can be structured multiphase liquids or isotropic liquids and which can be aqueous or non-aqueous liquids. These liquids can be in bottles or unit dose sachets and they can optionally contain bleaching agents or enzymes (reference can be made for example to U.S. Pat. Nos. 5,929,022, 5,916,862, 5,731,278, 5,470,507, 5,466,802, 5,460,752, and 5,458,810).

The products presently disclosed can contain water and/or surface-active material, either as an emulsifier, if the product is an emulsion, or as a detergent active material if the product has some kind of cleaning function. In certain embodiments the concentration of surface active material in the product will be within the range 0.1-60% by weight; usually the level of surface active material will be 50% by weight or lower; for most products the level of surface active material will be 30% by weight or lower. On the other hand, the level of surface active material will usually be at least 0.1% by weight, sych as but not limited to greater than 1.0% or greater than 3.0% by weight. Certain product formulations are water sensitive (e.g., anti-perspirant, deodorant formulations, non-aqueous liquids packaged in water soluble polyvinyl alcohol films), and for these applications it can be desirable to spray dry the microcapsules to remove water, before the microcapsules are incorporated in the product formulation. For products which have a cleaning function it is likely the level of surface-active material will be higher, typically greater than 10% by weight or greater than 15% by weight. All percentages are expressed by weight over the weight of the product.

Examples of leave-on products containing emulsifiers are: hand and body lotions, make up removing lotions, skin creams, sunscreen products and sunless tanning products and domestic freshener sprays. Also included are articles of manufacture impregnated with liquids, for example pads or wipes impregnated with lotions for make-up application or removal, or to apply sunscreen compounds or sunless tanning agents, for personal cleansing e.g., as moist toilet tissue or baby wipes.

Examples of personal cleansing products containing detergents are: shampoos, body washes, liquid soaps. Some cleaning products can be considered leave on products even though they are used for cleansing if there is no rinsing or further cleaning action after use. Baby wipes are an example, although used for cleaning the liquid deposited on the skin is not removed by rinsing.

The non-rinsed cosmetic, toiletry and personal care compositions described herein can contain various emulsifiers which are useful for emulsifying the various components of the products. Suitable emulsifiers can include any of a wide variety of non-ionic, cationic, anionic, and zwitterionic surface active materials as disclosed in publications such as McCutcheon's, Detergents and Emulsifiers, North American Edition (1986), published by Allured Publishing Corporation and in the following patents: U.S. Pat. Nos. 5,011,681; 4,421,769; and 3,755,560.

When the various consumer products described above contain a fragrance composition of the present disclosure in encapsulated form, the amount of microcapsules dosed into said products can vary depending on several aspects such as the desired microcapsule concentration, the proportion of fragrance within the microcapsules and the amount of fragrance necessary to create the olfactory effect desired. After removing all liquid components from a given product (i.e., measured as dry weight) the microcapsules can be present in an amount from about 0.01 to about 10.00% by weight, such as but not limited to from about 0.05% to about 2.50% by weight, or from about 0.10 to about 1.25% by weight over the weight of the product. The dispersion of microcapsules can be incorporated at a suitable stage in the product manufacturing process but usually after any high shear mixing stage. In certain embodiments, when the product is liquid at room temperature, the product into which the microcapsules are to be added can have a viscosity greater than about 20 MPa, for example greater than about 100 MPa, or greater than about 1,000 MPa, or even greater than about 10,000 MPa, when measured at a low (e.g., 10 rpm) spindle speed and at 25° C. If necessary, viscosity can be adjusted through the addition of conventional viscosity modifying agents. Suitable agents as well as equipment and conditions to measure the viscosity of a product are discussed in Rheology Modifiers Handbook Practical Uses and Applications by M R Rosen and D Braun published by William Andrew Publishing in 2000 with ISBN 978-0-8155-1441-1.

It has been found that when an accord as disclosed above is added to a fragrance composition (containing at least one fragrance compound other than the compounds of the accord), the intensity as well as the tingling and/or cooling effect of the fragrance composition are enhanced.

Accordingly, another aspect of the present disclosure relates to the use of an accord, when formulated into a fragrance composition, as an agent enhancing the intensity and/or the cooling effect and/or the tingling effect of the fragrance composition, wherein the accord includes:

(i) about 90.00 wt % to about 100 wt %, based on the weight of the accord, of a mixture of dihydromyrcene and at least one other compound selected from peppermint cyclohexanone, menthol, isopulegol, pulegol and menthyl acetate;

(ii) from about 0 wt % to about 10.00 wt %, based on the weight of the accord, of at least one compound selected from citroxide, elemicin, elemol, geranic oxide, vanillyl ethyl ether, vanillyl butyl ether, caryophyllene beta and zingiberene alpha;

wherein the sum of (i)+(ii) makes up 100 wt % of the accord.

The present disclosure is also directed to a method of enhancing intensity and/or cooling effect and/or tingling effect of a fragrance composition by adding to the fragrance composition an accord, which includes:

(i) about 90.00 wt % to about 100 wt %, based on the weight of the accord, of a mixture of dihydromyrcene and at least one other compound selected from peppermint cyclohexanone, menthol, isopulegol, pulegol and menthyl acetate;

(ii) from about 0 wt % to about 10.00 wt %, based on the weight of the accord, of at least one compound selected from citroxide, elemicin, elemol, geranic oxide, vanillyl ethyl ether, vanillyl butyl ether, caryophyllene beta and zingiberene alpha;

wherein the sum of (i)+(ii) makes up 100 wt % of the accord.

In certain embodiments, the accord includes from about 90.00 wt % to about 100 wt %, from about 92.00 wt % to about 100 wt %, from about 95.00 wt % to about 100 wt % from about 98.00 wt % to about 100 wt % based on the weight of the accord, of a mixture of dihydromyrcene and at least one other compound selected from peppermint cyclohexanone, menthol, isopulegol, pulegol and menthyl acetate. In certain embodiments, the accord includes about 90.00 wt %, about 92.00 wt %, about 95.00 wt %, about 98.00 wt % or about 100 wt % based on the weight of the accord, of a mixture of dihydromyrcene and at least one other compound selected from peppermint cyclohexanone, menthol, isopulegol, pulegol and menthyl acetate.

In certain embodiments, the accord includes from about 0.01 wt % to about 10.00 wt %, from about 0.50 wt % to about 10.00 wt %, from about 1.00 wt %, to about 10.00 wt %, from about 1.50 wt %, to about 10.00 wt %, from about 2.00 wt %, to about 10.00 wt %, from about 2.50 wt %, to about 10.00 wt %, from about 5.00 wt %, to about 10.00 wt %, from about 7.50 wt % to about 10.00 wt %, from about 9.00 wt %, to about 10.00 wt %, from about 0.01 wt % to about 9.00 wt %, from about 0.01 wt % to about 7.50 wt %, from about 0.01 wt % to about 5.00 wt %, from about 0.01 wt % to about 2.50 wt %, from about 0.01 wt % to about 1.50 wt %, from about 0.01 wt % to about 1.00 wt %, based on the weight of the accord, of at least one compound selected from citroxide, elemicin, elemol, geranic oxide, vanillyl ethyl ether, vanillyl butyl ether, caryophyllene beta and zingiberene alpha.

In certain embodiments, the amount of dihydromyrcene and at least one other compound selected from peppermint cyclohexanone, menthol, isopulegol, pulegol menthyl acetate, citroxide, elemicin, elemol, geranic oxide, vanillyl ethyl ether, vanillyl butyl ether, caryophyllene beta and zingiberene alpha makes up 100 wt % of the accord.

The present disclosure will be better understood in the light of the following examples given by way of illustration only. In these examples the percentages expressed are percentages by weight unless otherwise mentioned.

EXAMPLES

The present application is further described by means of the examples, presented below, wherein the abbreviations have the usual meaning in the art.

The use of such examples is illustrative only and does not limit the scope and meaning of the disclosed subject matter or of any exemplified term. Likewise, the disclosed subject matter is not limited to any particular preferred embodiments described herein. Indeed, many modifications and variations of the disclosed subject matter are apparent to those skilled in the art upon reading this specification. The disclosed subject matter is therefore to be limited only by the terms of the appended claims along with the full scope of equivalents to which the claims are entitled.

In the following fragrance compositions, lime oxide containing about 9.7 wt % citroxide was obtained from the company Ventos; dimene containing about 20.0 to about 40.0 wt % dihydromyrcene was obtained from the company Bordas.

Example 1

Fragrance Composition 1

Example 1 provides an exemplary "base" fragrance composition according to certain embodiments of the present disclosure. This "base" fragrance composition has a 4% hole, marked as "Additional Compound(s)" in Table 1.

TABLE 1

| Fragrance Composition 1 | | |
| --- | --- | --- |
| Ingredient Name | CAS No. | Wt % |
| Decanal | 112-31-2 | 2.18 |
| Benzyl acetate | 140-11-4 | 6.55 |
| Citronellal | 106-23-0 | 2.18 |
| Citronellol 950 | 106-22-9 | 7.54 |
| Citronellyl nitrile | 51566-62-2 | 4.37 |
| Cyclacet | 54830-99-8 | 4.37 |
| Cyclamen aldehyde Extra | 103-95-7 | 2.18 |
| Dihydromyrcenol | 18479-58-8 | 11.79 |
| Dipropylene Glycol | 25265-71-8 | 3.28 |
| Hexyl Cinnamic Aldehyde | 101-86-0 | 5.46 |
| Lemon Oil Italian | 8008-56-8 | 3.71 |
| Lime oil terpenes | 68917-71-5 | 3.28 |
| Linalool synthetic | 78-70-6 | 13.11 |
| Ethylene brassylate | 105-95-3 | 3.50 |
| Orange Oil 10 fold | 8008-57-9 | 3.93 |
| Styrallyl acetate | 93-92-5 | 4.37 |

TABLE 1-continued

Fragrance Composition 1

| Ingredient Name | CAS No. | Wt % |
|---|---|---|
| Terpineol | 98-55-5 | 3.50 |
| Terpinyl acetate | 80-26-2 | 4.37 |
| Verdox | 88-41-5 | 6.33 |
| Additional Compound(s) | | 4.00 |
| Total | | 100.00 |

Example 2

Fragrance Composition 2

Example 2 provides an exemplary fragrance composition according to certain embodiments of the present disclosure. This particular fragrance composition was prepared by adding 4.0 wt % dipropylene glycol (DPG) as an "additional compound" in the fragrance composition of Example 1.

Example 3

Fragrance Composition 3

Example 3 provides an exemplary fragrance composition according to certain embodiments of the present disclosure. This particular fragrance composition was prepared by adding 1.9 wt % dimene, 1.9 wt % peppermint cyclohexanone and 0.2 wt % lime oxide as "additional compounds" in the fragrance composition of Example 1.

Example 4

Fragrance Composition 4

Example 4 provides an exemplary fragrance composition according to certain embodiments of the present disclosure. This fragrance composition was prepared by adding 2 wt % dimene and 2 wt % peppermint cyclohexanone as "additional compounds" in the fragrance composition of Example 1.

Example 5

Fragrance Composition 5

Example 5 provides This fragrance composition was obtained by making up fragrance composition an exemplary fragrance composition according to certain embodiments of the present disclosure. This fragrance composition was prepared by adding 2 wt % dimene and 2 wt % menthol as "additional compounds" in the fragrance composition of Example 1.

Example 6

Fragrance Composition 6

Example 6 provides an exemplary fragrance composition according to certain embodiments of the present disclosure. This fragrance composition was prepared by adding 1.9 wt % dimene, 1.9 wt % menthol and 0.2 wt % lime oxide as "additional compounds" in the fragrance composition of Example 1.

Example 7

Consumer Panel Test

Example 7 provides consumer panel test of certain fragrances according to the present disclosure. Test samples for the panellists were prepared by soaking wicks, used in electric air care devices, in solutions of the respective fragrance compositions, then putting the wicks into bottles for assessment by the panellists. The wicks were 6.1 mm in diameter and 25 mm long made from mixed polyethylene and polyethylene terephthalate fibres. One wick was added to a glass jar of 60 mL volume, sealed with plastic screw cap having a waxed cardboard insert. The samples were labelled with a code in order to be anonymous to the panellists.

The experiments were carried out as part of a consumer test concerning the addition of test compounds to fragrance compositions and testing the responses of typical consumers to various attributes of the resulting fragrance samples, such as perceived intensity and perceived tingling sensations in the nose. For this test a group of approximately 60 panellists were recruited between the age of 21 to 60 years old including approximately equal numbers of males and females. Fragrance compositions 2 to 6 were tested by each panellist with a randomised order of presentation. Panellists were asked to score the attributes on a line scale from 0 (absence of attribute) to 10, (very strong perception of attribute). Panellists were free to sniff the samples however they wanted for as long or short a period of time and could repeat sniffs if desired. There was a 2 minute gap between each sample presentation to a panellist to minimise fatigue and adaptation.

Panellists scores were converted to numbers values in an excel data file and analysed by Analysis of Variance (ANOVA) using Excelstat. The results given are the Least Squares Mean Panel Scores for the samples and attributes. The significance groups indicate statistically significant differences at the 95% confidence interval. The results are presented in Tables 2 and 3.

TABLE 2

Mean Scores for Perceived Fragrance Intensity

| Fragrance composition | Mean Score | Significance group |
|---|---|---|
| 2 | 3.4 | B |
| 3 | 4.5 | A |
| 4 | 4.0 | A/B |
| 5 | 4.2 | A/B |
| 6 | 4.6 | A |

As can be seen from Table 2, fragrance compositions 3 to 6 were perceived as stronger than fragrance composition 2 (control).

TABLE 3

Mean Scores for Perceived Tingling Sensation in the Nose

| Fragrance composition | Mean Score | Significance group |
|---|---|---|
| 2 | 2.0 | C |
| 3 | 4.3 | A |
| 4 | 3.0 | B |
| 5 | 3.6 | A/B |
| 6 | 4.0 | A/B |

As can be seen from Table 3, fragrance compositions 3 to 6 were perceived as giving a stronger tingling sensation than fragrance composition 2 (control).

Example 8

Fragrance Composition 7

Example 8 provides an exemplary "base" fragrance composition according to certain embodiments of the present disclosure, as shown in Table 4. This "base" fragrance composition has a 2% hole, marked as "Additional Compound(s)" in Table 4.

TABLE 4

Fragrance Composition 7

| Ingredient name | CAS No | Wt % |
| --- | --- | --- |
| Dipropylene glycol | 25265-71-8 | 17.2 |
| Benzyl acetate | 140-11-4 | 10.6 |
| Verdox | 88-41-5 | 10.6 |
| Cyclacet | 54830-99-8 | 10.6 |
| Dihydromyrcenol | 18479-58-8 | 6.4 |
| Tetrahydrolinalool | 78-69-3 | 4.3 |
| Ethylene brassylate | 105-95-3 | 2.7 |
| Patchouli ethanone | 54464-57-8 | 5.3 |
| Alpha isomethyl ionone | 127-51-5 | 4.3 |
| Hedione | 24851-98-7 | 9.6 |
| Lilial | 80-54-6 | 4.3 |
| Orange oil Pera Brazil Nat EO | 8008-57-9 | 2.1 |
| Floralozone | 67634-15-5 | 1.0 |
| Allyl amyl glycolate | 67634-00-8 | 1.6 |
| Cyclohexyl salicylate | 25485-88-5 | 2.1 |
| Hexyl acetate | 142-92-7 | 1.0 |
| Methyl anthranilate | 134-20-3 | 1.6 |
| 2-Phenyl ethanol | 60-12-8 | 2.7 |
| Additional Compound(s) | | 2.0 |
| Total | | 100.0 |

Example 9

Fragrance Composition 8

Example 9 provides an exemplary fragrance composition according to certain embodiments of the present disclosure. This particular fragrance composition was prepared by adding 2.0 wt % dipropylene glycol (DPG) as an "additional compound" in the fragrance composition of Example 8.

Example 10

Fragrance Composition 9

Example 10 provides an exemplary fragrance composition according to certain embodiments of the present disclosure. This particular fragrance composition was prepared by adding 0.95 wt % dimene, 0.95 wt % peppermint cyclohexanone and 0.1 wt % lime oxide as "additional compounds" in the fragrance composition of Example 8.

Example 11

Fragrance Composition 10

Example 11 provides an exemplary fragrance composition according to certain embodiments of the present disclosure. This particular fragrance composition was prepared by adding 1 wt % dimene and 1 wt % peppermint cyclohexanone as "additional compounds" in the fragrance composition of Example 8.

Example 12

Fragrance Composition 11

Example 12 provides an exemplary fragrance composition according to certain embodiments of the present disclosure. This particular fragrance composition was prepared by adding 1 wt % dimene and 1 wt % menthol as "additional compounds" in the fragrance composition of Example 8.

Example 13

Fragrance Composition 12

Example 12 provides an exemplary fragrance composition according to certain embodiments of the present disclosure. This particular fragrance composition was prepared by adding 0.95 wt % dimene, 0.95 wt % menthol and 0.1 wt % lime oxide as "additional compounds" in the fragrance composition of Example 8.

Example 14

Consumer Panel Test

Example 14 provides consumer panel test of certain fragrances according to the present disclosure. Test samples for the panellists were prepared by soaking wicks, used in electric air care devices, in solutions of the respective fragrance compositions, then putting the wicks into bottles for assessment by the panellists. The wicks were 6.1 mm in diameter and 25 mm long made from mixed polyethylene and polyethylene terephthalate fibres. One wick was added to a glass jar of 60 mL volume, sealed with plastic screw cap having a waxed cardboard insert. The samples were labelled with a code in order to be anonymous to the panellists.

The experiments were carried out as part of a consumer test concerning the addition of test compounds to fragrance composition and testing the responses of typical consumers to various attributes of the resulting fragrance samples, such as perceived intensity and tingling sensations in the nose. For this test a group of approximately 60 panellists were recruited between the age of 21 to 60 years old including approximately equal numbers of males and females. Fragrance compositions 8 to 12 were tested by each panellist with a randomised order of presentation. Panellists were asked to score the attributes on a line scale from 0 (absence of attribute) to 10, (very strong perception of attribute). Panellists were free to sniff the samples however they wanted for as long or short a period of time and could repeat sniffs if desired. There was a 2 minute gap between each sample presentations to a panellist to minimise fatigue and adaptation.

Panellists scores were converted to numbers values in an excel data file and analysed by Analysis of Variance (ANOVA) using Excelstat. The results given are the Least Squares Mean Panel Scores for the samples and attributes. The significance groups indicate statistically significant differences at the 95% confidence interval. The results are presented in Tables 5 and 6.

TABLE 5

Mean Scores for Perceived Fragrance Intensity

| Fragrance composition | Mean Score | Significance group |
|---|---|---|
| 8 | 3.7 | B/C |
| 9 | 4.0 | A/B/C |
| 10 | 4.3 | A/B/C |
| 11 | 3.7 | B/C |
| 12 | 4.0 | A/B/C |

As can be seen from Table 5, fragrance compositions 9 to 12 were perceived as stronger than or comparable to fragrance composition 8 (control).

TABLE 6

Mean Scores for Perceived Tingling Sensation in the Nose

| Fragrance composition | Mean Score | Significance group |
|---|---|---|
| 8 | 2.0 | C |
| 9 | 3.8 | A |
| 10 | 2.9 | A/B/C |
| 11 | 3.3 | A/B |
| 12 | 3.4 | A/B |

As can be seen from Table 6, fragrance compositions 9 to 12 were perceived as more tingling than fragrance 8 (control).

Although the presently disclosed subject matter and its advantages have been described in detail, it should be understood that various changes, substitutions and alterations can be made herein without departing from the spirit and scope of the application as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the device, method, and system of the disclosed subject matter without departing from the spirit or scope of the disclosed subject matter. Thus, it is intended that the disclosed subject matter include modifications and variations that are within the scope of the appended claims and their equivalents.

For any patents, patent applications, publications, product descriptions, and protocols are cited throughout this application, the disclosures of all of which are incorporated herein by reference in their entireties for all purposes.

The invention claimed is:

1. A fragrance composition comprising from about 0.10 wt % to about 15.00 wt %, based on the weight of the fragrance composition, of an accord, wherein the accord comprises:
   (i) from about 90.00 wt % to about 100 wt %, based on the weight of the accord, of a mixture of dihydromyrcene and at least one other compound selected from the group consisting of peppermint cyclohexanone, menthol, isopulegol, pulegol, menthyl acetate, and combinations thereof.

2. The fragrance composition of claim 1, wherein the accord further comprises:
   (ii) from about 0.01 wt % to about 10.00 wt %, based on the weight of the accord, of at least one compound selected from the group consisting of citroxide, elemicin, elemol, geranic oxide, vanillyl ethyl ether, vanillyl butyl ether, caryophyllene beta, zingiberene alpha, and combinations thereof; and
   wherein the sum of (i)+(ii) makes up 100 wt % of the accord.

3. The fragrance composition of claim 2, wherein the said at least one compound (ii) is selected from citroxide, elemicin, elemol and mixtures thereof.

4. The fragrance composition of claim 2, wherein the accord comprises citroxide, and
   wherein citroxide is present in the accord in an amount of from about 0.01 wt % to about 1.00 wt %, based on the weight of the accord.

5. The fragrance composition of claim 2, wherein the accord comprises dihydromyrcene, peppermint cyclohexanone, and citroxide.

6. The fragrance composition of claim 2, wherein the accord comprises dihydromyrcene, menthol, and citroxide.

7. The fragrance composition of claim 1, wherein the fragrance composition comprises from about 1.00 wt % to about 12.00 wt % of the accord.

8. The fragrance composition of claim 1, wherein the fragrance composition comprises from about 2.00 wt % to about 10.00 wt % of the accord.

9. The fragrance composition of claim 1, wherein the accord comprises at least about 5.00 wt % of dihydromyrcene, based on the weight of the accord.

10. The fragrance composition of claim 1, wherein the mixture (i) comprises dihydromyrcene and peppermint cyclohexanone.

11. The fragrance composition of claim 10, wherein the accord comprises at least about 40.00 wt % of dihydromyrcene and peppermint cyclohexanone, based on the weight of the accord.

12. The fragrance composition of claim 1, wherein the mixture (i) comprises dihydromyrcene and menthol.

13. The fragrance composition of claim 12, wherein the accord comprises at least about 40.00 wt % of dihydromyrcene and menthol, based on the weight of the accord.

14. The fragrance composition of claim 1, wherein the fragrance composition is encapsulated.

15. A consumer product comprising the fragrance composition of claim 1, wherein the consumer product is selected from the group consisting of a household product, a laundry product, a personal care product and a cosmetic product.

16. The household product of claim 15, wherein the household product is selected from the group consisting of an air freshener dispenser device, a floor cleaner and a solid or liquid toilet rim block.

17. The household product of claim 15, wherein the household product is an air freshener dispenser device.

18. The laundry product of claim 15, wherein the laundry product is selected from the group consisting of a laundry detergent, a laundry additive, a fabric conditioner, and a fabric softener.

19. A method to enhance intensity and/or the cooling effect and/or the tingling effect of a fragrance composition, the method comprising adding to the fragrance composition an accord comprising:

(i) from about 90.00 wt % to about 100 wt %, based on the weight of the accord, a mixture of dihydromyrcene and at least one other compound selected from the group consisting of peppermint cyclohexanone, menthol, isopulegol, pulegol, menthyl acetate, and combinations thereof.

20. The method of claim 19, wherein the accord further comprises:

(ii) from about 0.01 wt % to about 10.00 wt %, based on the weight of the accord, of at least one compound selected from the group consisting of citroxide, elemicin, elemol, geranic oxide, vanillyl ethyl ether, vanillyl butyl ether, caryophyllene beta, zingiberene alpha, and combinations thereof; and wherein the sum of (i)+(ii) makes up 100 wt % of the accord.

* * * * *